United States Patent [19]

Pusch et al.

[11] 3,956,350

[45] May 11, 1976

[54] PROCESS FOR THE PRODUCTION OF TEXTILE SOFTENERS

[75] Inventors: Günter Pusch, Leitershofen; Heinrich Singer, Horgau, both of Germany; Jutta Ibrahim, Allschwil, Switzerland

[73] Assignee: Ciba-Geigy Corporation, Ardsley, N.Y.

[22] Filed: Apr. 8, 1974

[21] Appl. No.: 458,923

[30] Foreign Application Priority Data
  Apr. 14, 1973  Germany............................. 2318906
  Jan. 18, 1974  Germany............................. 2402258

[52] U.S. Cl............................. 260/404.5; 252/8.8; 8/18 R
[51] Int. Cl.$^2$............. C07C 103/12; C07C 103/127; C07C 103/133
[58] Field of Search................................. 260/404.5

[56]  References Cited
  UNITED STATES PATENTS
  2,243,980  6/1941  Rheiner et al. ............... 260/404.5 X
  2,304,113  12/1942  Morgan et al. ............... 260/404.5 X
  2,304,369  12/1942  Morgan et al. ............... 260/404.5 X
  3,369,021  2/1968  LeSuer........................ 260/404.5 X Primary Examiner—Patrick P. Garvin
Attorney, Agent, or Firm—Joseph G. Kolodny; Edward McC. Roberts; Prabodh I. Almaula

[57]  ABSTRACT

This invention relates to the production of condensation products which can be used to impart a soft handle to textiles. A monobasic fatty acid with at least 8 carbon atoms and/or montanic acids is reacted with dipropylene triamine and/or diethylene triamine. At least 40 mol % of the acid must be a straight chain fatty acid with at least 12 carbon atoms. The molar ratio of fatty acid to triamine is about 2:1. Thereafter the resulting product is heated with urea in a molar ratio of product to urea of 1:0.5 to 1:1, and optionally the resulting urea condensate is treated with 1 to 5 moles of formaldehyde by mole of urea condensate. The final product can be made into an aqueous emulsion or organic solvent solution and used in the treatment of textiles to give an excellent and soft handle without yellowing of white textiles or changing the shade of coloured textiles.

4 Claims, No Drawings

PROCESS FOR THE PRODUCTION OF TEXTILE SOFTENERS

This invention relates to the production of condensation products and their uses.

BACKGROUND TO THE INVENTION

As described in German Patent Specification No. 697,803 condensation products can be prepared from higher fatty acids and polyvalent amines and one can additionally introduce into these products a carbonamide group as described in Patent of Addition No. 700,767. After further reaction with formaldehyde, these products are inter alia suitable as textile aids.

However, these products have a number of disadvantages. Thus, when they are used on textiles, they frequently cause a deterioration in the degree of whiteness of white fabrics and a shift in the colour tone of coloured fabrics. In addition the treated textile fabrics have persistent unpleasant odours. These odours can be avoided by employing relatively large quantities of catalysts for curing the products on the fabric, but as a result the strength of the fabric is impaired. Also, the resistivity to chlorine and the handle of fabrics so treated are unsatisfactory. Furthermore, when they are used jointly with synthetic resin products which initially contain N-methylol groups and which are for imparting a non-crease finish, these crease-resistant properties are impaired.

It is therefore, an object of this invention to avoid these disadvantages.

BRIEF DESCRIPTION OF THE INVENTION

According to the invention there is provided a process for the production of condensation products in which saturated and/or unsaturated, aliphatic, straight-chain and/or branched chain, monobasic fatty acids with at least 8 carbon atoms and/or montanic acids, with the proviso that at least 40 mole % consist of saturated or mono unsaturated, straight-chain fatty acids with at least 12 carbon atoms, more especially with at least 14 carbon atoms, and/or montanic acids, are reacted with diethylene triamine, dipropylene triamine or their mixtures in a molar ratio of acids to triamines of about 2:1 the resulting fatty acid amine condensation product which consists substantially of the bis-fatty acid amide of the triamine and which will hereinafter be referred to for brevity as "bis-fatty acid amide", is heated with urea in a molar ratio from 1:0.5 to 1:1 so that from 0.5 to 1 mole of $NH_3$ per mole of introduced bis-fatty acid amide is split off, and advantageously the resulting urea condensation product is then treated with 1 to 5 moles of formaldehyde per mole of urea.

The advantageously methylolated fatty acid condensation products which are thus produced can be used as solutions in organic solvents or preferably as aqueous emulsions for the treatment of fibre-like material, more especially textiles. They impart to such materials a soft, smooth surface handle without the disadvantages noted above.

Particularly advantageous results are obtained when the condensation products are used for treating polyamides, polyesters and polyacrylonitriles textile by the extraction or padding method. Not only is a soft handle obtained on these materials, but at the same time antistatic properties are obtained.

Saturated, unsaturated, aliphatic, straight-chain and branched-chain monobasic fatty acids with at least 8 carbon atoms are suitable acids for the production of the condensation products of the invention. These acids can also be used in admixture with one another. However, it is always to be borne in mind that fatty acids with fewer than 12 carbon atoms cannot be used by themselves and the mixtures must contain at least 40 mole % of fatty acids with at least 12 carbon atoms and more particularly with at least 14 carbon atoms. Examples of suitable acids are caprylic, capric, lauric, palmitic, stearic, arachic and behenic acids and also montanic acids. Oleic acid is a suitable example of unsaturated acid, while examples of fatty acid mixtures of synthetic fatty acids with a chain length from about 9 to 11 carbon atoms are acids having a branched chain, these mixtures containing about 10% of secondary acids and 90% of tertiary acids (SÖFW, 88 page 438 [1962.])

As already noted, the fatty acids used for the production of the condensation products of the invention must contain at least 40 mole % of saturated and/or ethylenically unsaturated, stright-chain fatty acids with at least 12 carbon atoms, more especially with at least 14 carbon atoms and/or montanic acids. This provision ensures that the condensation products which are produced therefrom, when applied to fibre material, give the required smooth-surface handle and in addition guarantee a sufficiently high resistance to sublimation. Furthermore, the required handle can be varied by the particular fatty acid chosen. Thus, for example, when using saturated fatty acids, such as stearic acid, a particularly soft, smooth-surface handle is produced, while the use of fatty acids having a shorter chain, such as lauric acid, and/or the use of unsaturated fatty acids, such as oleic acid, results in a voluminous handle having a less smooth surface.

Suitable amines for use in the production of the condensation products of the invention are diethylene triamine, dipropylene triamine or their mixtures. These amines contain two primary amino groups and one secondary amino group. Other polyalklene polyamines, as for example triethylene tetramine, which contains two secondary amino groups, are unsuitable for use in the process of the invention, since the condensation products using them can have the disadvantages noted above in connection with the prior art.

The fatty acids and the diethylene triamine and/or dipropylene triamine are reacted with one another in a molar ratio of about 2:1. They can be reacted in a manner known per se for making condensation products while heating and stirring, to give the corresponding bis-fatty acid amides. One can follow the progress of the reaction by the amount of water which distills off. Instead of using the fatty acids themselves, one can also use their esters with lower alcohols in which case the corresponding alcohols will distill off during the condensation with the triamines.

Into the melt, which is preferably cooled to below 130°C, 0.5 to 1 mole and preferably 0.5 to 0.75 mole of urea per mole of bis-fatty acid amide is then slowly introduced while stirring, ammonia being given off on renewed heating to about 130° to 140°C. As soon as the evolution of ammonia slows down, which is usually the case after about 2 to 3 hours, the temperature is increased to about 180°C to complete the removal of the ammonia. It is also desirable to work under reduced pressure towards the end of the ammonia removal or sustantially to flush away the ammonia dissolved in the condensation product by passing an inert gas through the melt of the said product.

A maximum of 1 mole of ammonia can be given off, both when the molar ratio of bis-fatty acid amide urea is 1:0.5 and when it is 1:1. However, it is not necessary for the theoretical maximum quantity of ammonia to be given off. Thus, products suitable for use are already obtained when about 50% and more especially 70% of the thus amount of ammonia has been removed.

Products which are particularly suitable for use are obtained when the bis-fatty acid diamide-urea condensates are also treated in the usual way with 1 to 5 moles of formaldehyde per mole of urea.

The products which are produced according to the invention differ in many repsects from the products of the prior art. One essential feature of the products which are produced by the process of the invention is that the fatty acids and the dialkylene triamine are reacted in the first stage of the reaction in a molar ratio of around 2:1, whereas a ratio of about 1:1 is always used in this stage in accordance with the said prior art. It s also important that only diethylene triamine and/or dipropylene triamine, which contain two primary amino groups and only one secondary amino group, be used as the polyalkylene polyamines in the process according to the invention, whereas other polyalkylene polyamines i.e. amines with two and more secondary amino groups, but especially triethylene tetramine, are quite generally used according to the prior art.

As is clear from these statements, the fatty acid amides condensates which are obtained according to the prior art still contain at least two free basic hydrogen atoms which are bonded on nitrogen atoms and of which one is thereafter substituted by a carbonamide group. In contrast thereto, the bis-fatty acid amides obtained according to the invention in the first reaction stage still only contain one secondary hydrogen atom bonded to nitrogen. After the condensation of these amides with urea, there is consequently no longer a basic hydrogen atom bonded to nitrogen. As already mentioned, condensates with urea which are preferred in the process according to the invention are those which are obtainable by condensation of 1 mole of bis-fatty acid amide with 0.5 to 0.75 and more especially with 0.5 mole of urea, so that in the latter case, assuming a complete reaction, theroretically compounds are formed which also no longer contain any free carbonamide groups. This will not be explained by reference to an example:

The reaction product of stearic acid and diethylene triamine (first stage) and urea (second stage) in the molar ratio of 4:2:1 would consequently theoretically have the following structure:

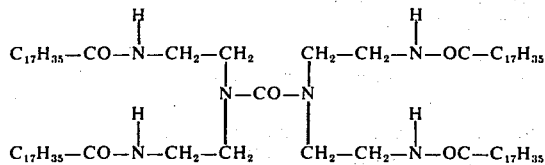

Since, however, the amount of ammonia to be theoretically expected does not have to be given off in the reaction between bis-fatty acid amide and urea, and moreover since those condensation products in which the reaction ratio between bis-fatty acid amide the urea can be 1:1 are also suitable the condensation products obtained according to the invention can have free carbonamide groups present.

The condensation products of the bis-fatty acid amide and urea can, if desired, be methylolated with formaldehyde. Proportionally more formaldehyde can be bonded in the form of N-methylol groups as there are more free carbonamide groups present in the condensation products before methylolation, it also being possible to a certain extent for formladehyde in looser form to be added to the hydrogen atoms of the fatty acid-carbonamide groups. Since it is a question in the latter case of an equilibrium reaction, the formaldehyde is usually not completely bonded, but this does not result in any disadvantageous properties in the end products.

As compared with the non-methylolated compounds, the N-methylol compounds have the additional advantage that the textiles treated therewith have a particularly good surface smoothness and the emulsions prepared from these methylolated condensation products by adding emulsifiers have a liquid consistency in a normal commercial concentration of about 25% at room temperature, whereas the corresponding emulsions of the non-methylolated condensation products have a higher viscosity and can even be of pasty nature.

The condensation products can be used in the form of solutions in organic solvent, examples of which are tetrachlorethylene, trichlorethylene or petroleum hydrocarbons for the treatment of fibre-like materials. However, the use in the form of aqueous emulsions is preferred. To this end, the condensation products can be emulsified in the usual way into emulsions by means of non-ionic or cationic emulsifiers or mixtures thereof. The ethoxylation products of alkyl phenols, fatty-acids, fatty acid amides and more especially of fatty alcohols are suitable emulsifiers for this purpose. Examples are octyl phenol polyglycol ethers with 5 to 20 bonded ethoxy groups, fatty acid polyglycol ethers with 10 to 100 bonded ethoxy groups or advantageously fatty alcohol with 5 to 100 bonded ethoxy groups, as non-ionic emulsifiers and octadecyl oxymethyl pyridinium chloride as a cationic emulsifier.

The amount of emulsifier depends on the type of the emulsifier and the properties which are required of the emulsion. It can vary within wide limits between 5 and 60% of the weight of the condensation product, depending on the type of emulsifier and the required properties.

It is desirable to adjust the resulting emulsions to a pH of from 3 to 7 by adding acids. Suitable acids are inorganic acids, such as hydrochloric acid, or preferably organic monobasic or dibasic acids with 1 to 6 carbon atoms, such as acetic acid, maleic acid or glycolic acid. The stability of the emulsions into presence of catalysts and metal salts is improved by this addition of acid.

The condensation products can be applied to fibres by padding and also be extraction.

When the former process is used, the materials can be impregnated with a solution which contains 5 to 50 g/l of the approximately 15 to 25% aqueous emulsion (based on condensation product), squeezed out to a solution absorption of 60 to 80% and then dried.

If the latter process is used, then of the approximately 15 to 25% aqueous emulsions with a solution ratio from 1:5 to 1:40, about 0.5 to 4% based on weight of material, can be used. The bath temperature should be at 30° to 40°C and the treatment time at 15 to 40 minutes unless the product is simultaneously dyed. With the extraction method, the pH should be 4 to 7, and preferably 4 to 6. Thereafter, the material is extracted for a short time and dried.

It is particularly advantageous with the extraction process to work in the dye bath. It is in fact possible for the aqueous condensation product emulsion either to be added directly to the dye bath or to be introduced following the dyestuff into the dye bath, and in this way to achieve the desirable soft, smooth-surface handle and antistatic properties in a single operation together with the dyeing.

If the condensation product is introduced simultaneously with the dyestuff, then approximately the following working procedure is desirable.

As well as the dyestuff, the usual additives, such as Glauber's salt, acetic acid and retarder, are introduced together with the aqueous emulsion of the condensation product into the bath solution and, with the previously mentioned bath solution ratios, there is obtained the simultaneous dyeing and improvement in handle, when the solution is heated up within 20 to 40 minutes to above 90°C, and kept at this temperature for another 1 to 2 hours. The material is then finished by rinsing, extracting and drying. If any processing follows the dyeing, the final finishing should be effected as described above in connection with the extraction method.

When using the padding process it is obviously also possible to use the emulsions of condensation products to the invention in combination with other products which are normal for the treatment of fibre-like material. Likewise, the emulsions of the products of the invention can also be combined before being used with other conventional emulsions, such as with emulsions which are based on organopolysiloxanes, polyethylene, paraffin and other polymers, e.g. polyacrylates, which exist in emulsion form. When the fibre-like material is a textile, the emulsions of the products of the invention can be used in combination with agents which increase crease resistance.

Organic solutions of the products of the invention can be used in a similar manner to the aqueous emulsions. Nevertheless, it is necessary to bear in mind here the concentration of the organic solution of condensation product, and once again it is possible to start from the basis that, of an approximately 15 to 25% solution, 5 to 50 g/l are used in the padding method and 0.5 to 4% in the extraction method, these figures being based on the weight of material.

Examples of suitable fibre-like materials are paper, leather and in particular textiles, which can be in the form of woven or knitted fabrics or fleeces. They can consist of natural of synthetic fibres or mixtures of such fibres. Excellent results are achieved when treating textiles consisting of or including polyamides, polyester, polyacrylonitriles in the form of yarns, woven fabrics, fleeces or knitwear. A particularly soft and pleasing handle is obtained when the textile consists of or includes polyacrylonitrile fibres. In addition to the soft and smooth-surface handle which the condensation products of the invention give to treated textiles, the textiles are simultaneously given an antistatic finish, particularly those which contain or consist of synthetic fibres. That antistatic properties are given could not be readily anticipated. For best results, preferably the methylolated fatty acid condensation prodcuts are used when treating synthetic materials. According to the prior art, antistatic properties are in fact obtained by the polyalkylene glycol residues which are present. However, these residues, disregarding small amounts of emulsifier, are not present in the condensation products according to the invention and consequently it is surprising according to the invention for textiles to be given antistatic properties together with an improvement in handle.

It is also advantageous that the final finishing can be carried out in one working step together with dyeing. Above all, however, the disadvantages of the prior art, which consist mainly in a deterioration in the degree of whiteness with white materials, a shift in the colour tone with coloured materials, the apperarance of unpleasant odours and the unsatisfactory loss in handle, are avoided.

PRESENTLY PREFERRED EMBODIMENTS OF THE INVENTION

The invention will now be illustrated by the following examples.

EXAMPLE 1

568 g of stearic acid (2 moles) were melted at 100°C in a three-necked spherical glass flask equipped with a stirrer device, thermometer and distillation condenser and 104 g of diethylene triamine (1 mole) were added over 20minutes by way of a supply vessel. The mixture was heated while stirring to reach 160°C within 1 hour and 180°C within approximately another hour. 2 This temperature was then maintained for about 30 minutes until about 38 g of water of condensation had distilled off and the acid number was below 5.

The resulting bis-fatty acid amide was neither soluble in cold or hot water nor dispersable therein without adding an emulsifier. It was cooled to 100°C and 30 g of urea (half mole) were stirred in three portions within 15 minutes. The temperature was thereafter slowly raised to 130° to 140°C, and ammonia began to be given off. The temperature of 140°C was maintained for about 2½ hours.

In order to remove from the reaction mass the remainder of the ammonia it was heated for 80 minutes to 180°C and suction filtering was carried out under a slight vacuum. A small sample was cooled to room temperature. The product has a firm, brittle nature and cold neither be dissolved nor dispersed in water. Its melting point was 68° to 70°C.

60 g of paraformaldehyde (2 moles) were then incorporated by stirring in portions into the melt which has been cooled to about 100°C and the temperature was again slowly raised to 140°C and maintained for 5 to 10 minutes. After this reaction, which is not a polycondensation, but merely an addition of formladehyde, there existed a yellowish clear melt, which solidified on cooling into a solid, brittle substance, which had a melting point of about 67°C, this was called product A.

In order to produce about 3 kg of a liquid and stable emulsion which is excellently suitable as a softener for textiles, 180 g of an alkyl polyglycol ether (the addition product of 40 moles of ethhylene oxide with 1 mole of fatty alcohol with 16 to 18 carbon atoms) were melted into 620 g of the condensation product as described above. Into this melt, which was at a temperature of 100° to 105°C, 800 g of hot water at about 70°C were added in a thin jet while stirring. The temperature during this time was not allowed to fall below 75°C. After adding the water, the mixture was heated to 90° to 95°C and the mixture is stirred for 40 to 60 minutes at this temperature to homogenise it. It was then cooled to 60°C and another 1400 g of cold water are stirred in.

The emulsion had a pH of 7 to 8 and was further cooled to about 30°C. Finally, it was adjusted to a pH of about 4.5 by stirring in 40 g of glycolic acid (57%). This emulsion is hereafter caled emulsion A, and is according to the invention.

For comparison purposes, a product B was prepared according to German Patent 697,803 and Patent of Addition 700,767 as follows.

284 g of stearic acid (1 mole) were melted in the apparatus as described above and 114 g of diethylene triamine (about 1.1 mole) were allowed to run slowly into the apparatus. The mixture was heated while stirring, first of all to 160°C and then within 1 hour to 180°C. This temperature was maintained until about 1 mole of water of condensation had distilled off. After cooling to about 100°C the amide which had formed 30 g of urea were stirred in and the temperature was once again slowly raised to 130° to 140°C. With ammonia being given off, a temperature of about 140°C was maintained for 2 hours, this being followed by heating within 80 minutes to 180°C and filtering off with suction under a light vacuum. A small sample of this condensation product was removed and cooled to room temperature. The product had good dispersing properties in hot water.

After cooling the batch to 70°C, 60 g of paraformaldehyde were added and the temperature was again raised to 110°C; hydrochloric acid was added to acidify the mixture, the temperature was kept for another 10 minutes at 110°C, and as a result an insoluble polycondensate was obtained.

After this reaction, there was present a brown melt of a fat-modified N-methylolamide polycondensate. The melt solidified on cooling into a resinous, solid, insoluble compound, which has a softening point of about 98° to 102°C and could not be dispersed in hot water, it will be called Product B.

This product B was emulsified in the same way as described in connection with product A to give emulsion B. The two emulsions A and B were tested as softening agents, these emulsions both being applied in the usual manner both to a mercerised, bleached and optically brightened cotton poplin (weight per square meter 126 g) and to a dyed 67/33 polyester/staple rayon twill (weight per square meter 190 g) by impregnation and squeezing out to a solution absorption of 65%. In fact two solutions of each emulsion were used.

| Solution 1 | 1 liter of water, containing 40 g of emulsion A or emulsion B |
| --- | --- |
| Solution 2 | 1 liter of water, containing 40 g of emulsion A or emulsion B, 60 g of dimethylol ethylene urea and 15 g of magnesium chloride hexahydrate. |

After the padding operation, the textiles were dried at 130°C and, in the case both solutions 2, further condensation thereafter took place for 4 minutes at 150°C.

After being laid out for a period of 48 hours, the cotton poplin was tested for its handle, yellowing, fish odour, crease angle and chlorine yellowing, while the polyester/staple rayon twill was merely tested for handle, since the other tests are not critical with this fabric on account of the dyeing and nature of the woven fabric.

The superiority of the emulsion according to the invention can be seen from the results given in the following Tables.

Solution 1

| | Cotton poplin | | | | Polyester/staple rayon twill | |
| --- | --- | --- | --- | --- | --- | --- |
| Emulsion | Original | handle after 1 wash at 60°C | Yellowing | Fish Odour | Original | handle after 1 wash at 60°C |
| A | 10 | 6 | none | none | 9 | 7 |
| B | 4 | 3 | obvious | some | 4 | 3 |

Solution 2

| | Cotton poplin | | | | | Polyester/staple rayon twill |
| --- | --- | --- | --- | --- | --- | --- |
| Emulsion | handle | yellowing | fish odour | crease (average angle of weft and warp) | chlorine yellowing after chlorinating and scorching acc. to AATCC | handle |
| without emulsion | 1 | none | none | 125° | none | 1 |
| A | 9 | none | none | 135° | none | 9 |
| B | 3 | obvious | strong | 122° | some | 3 |

In these Tables, the handle is given a value of 1 to 10, the value 1 being the handle without emulsion of softening agent and 10 representing an extremely soft and smooth surface handle.

EXAMPLE 2

216 g of industrial coconut fatty acid (1 mole) with an acid number from 250 to 260 and a saponification number from 251 to 261, and 284 g of stearic acid (1 mole), were melted together in a three-necked spherical flask provided with a stirrer, thermometer and distillation condenser and reacted with 104 g of diethylene triamine (1 mole), as described in Example 1. Once the acid number was below 5, the mixture was cooled to 100° to 110°C and 60 g of urea (1 mole) were added and the temperature was kept for about 2½ hours at 140°C. The temperature was then raised to 180°C and the ammonia still present in the product was purged with suction or driven off by injecting nitrogen. After cooling, a hard condensation product was obtained, which are very suitable as an initial product for the preparation of a softening agent or a finishing agent for fibrous materials.

The aforementioned industrial coconut fatty acid contains about 2% of capric acid, 52% of lauric acid, 22% of myristic acid, 10% of palmitic acid, 3% of stearic acid and 11% of oleic acid (amounts as a percentage by weight).

EXAMPLE 3

In an apparatus as described in Example 1, 424 g of stearic acid (about 1½ moles) and 162 g of behenic acid (0.5 mole) with an acid number from 162 to 166 were melted together and 104 g of diethylene triamine were slowly added at 110°C. Heating was carried out to 180° to C until there was an acid number below 5. As a result, about 40 g of distillate were obtained. The fatty acid amide was cooled to 100°C and 60 g (1 mole) of urea stirred in. The temperature was slowly raised to 140°and kept at this temperature for about 2 hours. The product was then heated to 180°C and, as described in Examples 1 and 2, the ammonia was removed from the reaction mass. After cooling, an extremely brittle condensation product was obtained. 680 g of the condensation product were melted with 260 g of an alkyl polyglycol ether (addition product of about 80 moles of ethylene oxide and 1 mole of fatty alcohol with 16 to 18 carbon atoms) at 100° to 110°C and then 90 g of paraformladehyde were stirred into the melt. The mixture was heated to 140°C, which was maintained for 15 minutes. The reaction mixture was then cooled to 100° to 105°C and 1100 g of hot water at about 75°C were added in a thin jet while stirring. The temperature did not fall below 85°C while this water was being added. After adding the water, the emulsion formed was heated to 90° to 95°and vigorously stirred for about 60 minutes. It was then quickly cooled to 60°C and another 1300 g of cold water added. Finally, the emulsion was adjusted with about 30 g of acetic acid to a pH value of 4.

The condensation product in this emulsion had outstanding properties as a softener or plasticiser and antistatic agent in the form of an aqueous emulsion which remains liquid to about 0°C, imparted a very soft and smooth handle to textiles and had a high resistance to sublimation.

EXAMPLE 4

325 g of industrial coconut palm kernal oil fatty acid with an acid number from 248 to 258 and a saponification number from 249 to 259 were melted with 200 g of montanic acid with an acid number from 120 to 140 and a saponification number from 140 to 160 and 132 g of dipropylene triamine (1 mole) were slowly added. The mixture wa heated to 190°C until the acid number was below 5. The mixture was then quickly cooled to 100°C and 45 g of urea added and condensed as described in Example 1, followed by further reaction with 90 g of paraformaldehyde after cooling to 100°C.

After cooling, there was present a brittle condensation product. To process this to a convenient aqueous emulsion, the selected emulsifier, advantageously in alkyl polyglycol ether, was simultaneously melted in the condensation product and the melt C was stirred into initially supplied water (70° to 80°C). For homogenisation, the emulsion was heated to 90° to 95°C and stirred for about 30 minutes. It was then quickly cooled, possible diluted with cold water to the required concentration and adjusted with hydrochloric acid to a pH value of 6.

The emulsion as thus prepared and adjusted, for example, to a solid content of 25%, already in a concentration of 20 to 30 g/l and with a usual solution absorption of 60 to 80%, related to the dry textile imparts to textiles a pleasing, soft, smooth surface handle, improves the tearing and abrasion resistance thereof and, more especially with woven and knitted fabrics containing synthetic fibres, improves the sewing ability of the latter.

The aforementioned coconut palm kernel oil fatty acid contains about 2% of capric acid, 51% of lauric acid, 16% of myristic acid, 10% of palmitic acid, 3% of stearic acid and 17% of oleic acid (amounts being in percentages by weight).

EXAMPLE 5

In the apparatus as described in Example 1, 173 (1 g mole) of capric acid and 284 (1 mole) of stearic acid were melted together and 132 g of dipropylene triamine were slowly added at 100° to 120°C. The mixture was heated to 180° to 190°C until it has an acid number below 5. In this case, a distillate of about 38.0 g was obtained. The mixture was then quickly cooled to 100°C and 30 g of urea (0.5 mole) were stirred in and condensation occurred as already described in the above examples with ammonia being split off. After condensation, the mixture was cooled once again to 90° to 100°C and methylolation was effected with 45 g of paraformaldehyde.

For the prepartion of a convenient emulsion, 160 g of an alkyl polyglycol ether (the addtion product of about 30 moles of ethylene oxide with 10 mole of fatty alcohol having 12 to 10 carbon atoms) were melted in and then, at 90° to 100°C and with stirring, 1000 g of hot water at 70°C were added in a thin jet and in such a way that the temperature did not fall below 70° to 75°C. For complete homogenisation, the emulsion was further heated for about 30 to 60 minutes to 90° to 95°C, cooled to 60°C and diluted with another 1200 g of cold water. The emulsion was adjusted with about 36 g of glycolic acid (57%) to a pH of 4.

EXAMPLE 6

104 g of diethylene triamine were introduced into 564 g (2 moles) of oleic acid at 80° to 90°C and, while splitting off water, the mixture was heated to 190°C until it had an acid number below 5 (distillate about 39 g). The mixture was then cooled to 100°C and, as already described, condensed with 40 g of urea, with ammonia being split off, at 140° to 190°C. For the better removal of the ammonia from the reaction mass, suction filtering took place. The product was then cooled to 90°C, reacted with 60 g of paraformaldehyde at 120° to 140°C and adjusted with about 10 g of phosphoric acid (85%) to a pH from 5.0 to 6.0. It is desirable to determine beforehand the amount of phosphoric acid required to give this pH by using a small sample of the condensation product to which hot water is added in the ratio of 1:5.

(pH 4 to 5 ), which contain $x\%$ of the condensation product emulsion described in Example 1. The treatment took place in a bath solution ratio of 1:30 at a temperature of 40°C for 30 minutes, whereafter the material was extracted for a short time and dried at 80°C. The excellent results obtained according to the invention are listed in the following Table together with the results of the untreated textile.

| textile | concentration "x" (%) | Statometer charging (volts/ cm) rubbed with wool | half-life decomposition time (sec) after rubbing with wool | megohmmeter surface resistance ($\Omega/cm^2$) | handle |
| --- | --- | --- | --- | --- | --- |
| polyamide tricot | 0 | 20500 | 140 | $5.4.10^{16}$ | = |
|  | 3.0 | 5000 | 82 | $1.3.10^{15}$ | ++ |
| polyacrylonitrile tricot | 0 | 48750 | 163 | $2.8.10^{16}$ | = |
|  | 1.0 | 16400 | 32 | $2.5.10^{14}$ | +++ |
|  | 2.0 | 16400 | 28 | $6.8.10^{13}$ | ++++ |
| polyester woven fabric | 0 | 28500 | 123 | $1.8.10^{16}$ | = |
|  | 1.0 | 9500 | 15 | $4.1.10^{14}$ | ++ |
|  | 2.0 | 8000 | 12 | $1.2.10^{14}$ | ++ |

In this table, was given a value in the following scale:
=      as untreated
+      trace of softness
++     distinct soft handle
+++    good soft handle
++++   very good soft handle For the application to textiles and leather from a solvent, such as for example tetrachlorethylene, and for better handling, the condensation product as thus obtained was dissolved in this solvent at a concentration of about 25%. When the 25% product as thus obtained was used in an amount of 40 g per liter of organic solvent on articles of clothing by impregnation, extracting (solution absorption about 70%) and drying, these garments were given a particularly soft smooth-surface handle. No change in colour tone and no unpleasant odour cold be detected.

EXAMPLE 7

A polyamide tricot (fixed, bleached and shrunk; weight 234 g/m²) of highly crimped polyamide yarns, a polyester woven fabric (washed and fixed, weight 200 g/m²) of texturised polyester endless yarn and a polyacrylonitrile tricot (untreated; weight 200 g/m²) were treated by the extraction method with bath solutions While the electrostatic behaviour was determined by measuring the charge (volts/cm) after rubbing with wool on the statometer according to R. Hase and measuring the half-life decomposition times (seconds) of the applied charges; and establishing the specific surface resistivity ($\Omega/cm^2$) with a high resistance meter (4329 A) A) (Hewlett-Packard).

EXAMPLE 8

The polyamide tricot mentioned in Example 7 and a polyacrylonitrile staple woven fabric (washed and bleached; weight 138 g/m²) and a polyester staple woven fabric (fixed and bleached: weight 130 g/m²) were impregnated with a bath solution containing 5, 10 and 20 g/l of the condensation product emulsion prepared in Example 5, squeezed out to 64% solution absorption and dried at 80°C. The results obtained are given in the following Table, in which for comparison purposes the value for an untreated specimen is also given.

| textile | concentration (g/l) | Statometer charge (volts/cm) after rubbing with wool | half-life decomposition time (sec) after rubbing with wool | megohmmeter surface resistivity $\Omega/cm^2$ | handle (evaluated as in Example 7) |
| --- | --- | --- | --- | --- | --- |
| polyamide tricot | 5 | 3000 | 45 | $6.0.10^{14}$ | ++ |
|  | 10 | 0 | 0 | $2.3.10^{14}$ | +++ |
|  | 20 | 750 | 1 | $1.9.10^{14}$ | +++ |
|  | 0 | 20500 | 140 | $5.4.10^{16}$ | = |
| polyacrylonitrile staple woven fabric | 5 | 7500 | 3 | $5.6.10^{14}$ | +++ |
|  | 10 | 3000 | 2 | $1.9.10^{14}$ | ++++ |
|  | 20 | 125 | 1 | $3.8.10^{13}$ | ++++ |
|  | 0 | 20000 | 58 | $9.4.10^{14}$ | = |
| polyester staple woven fabric | 5 | 1500 | 1 | $9.4.10^{12}$ | ++ |
|  | 10 | 400 | 1 | $3.0.10^{13}$ | ++ |
|  | 20 | 0 | 0 | $3.8.10^{13}$ | +++ |
|  | 0 | 10500 | 25 | $3.8.10^{15}$ | = |

EXAMPLE 9

A polyacrylonitrile high bulk yarn was simultaneously dyed and provided with a soft handle in the following manner.

The high bulk polyacrylonitrile yarn was treated with a bath solution which contained 1% of dyestuff (C.I. Basic Blue 22 ). 10% of Glauber's salt, 2% of 80% acetic acid, 1% of a retarder and $x$% of the condensation product emulsion prepared in Example 1, using the solution ratio of 1:30, the solution being first of all heated to 70°C, whereafter its temperature was raised within 30 minutes to 97°C and finally held for 90 minutes at this temperature. The yarn was thereafter, in the usual manner, rinsed, extracted and dried at 80°C. The results of these finishes were contained in the following Table, the dyeing of the high bulk yarn not having been influenced in any way by the finishing.

| concentration $x$ (%) | surface resistivity ($\Omega$/cm$^2$) | handle (evaluated as in Example 7) |
|---|---|---|
| 0% | $3.8 \cdot 10^{15}$ | = |
| 0.5% | $2.8 \cdot 10^{13}$ | +++ |
| 1.0% | $2.8 \cdot 10^{12}$ | ++++ |

What we claim is:

1. A process for the production of textile softeners, comprising the steps of condensing with stirring and heating an aliphatic monobasic fatty acid of at least 8 carbon atoms or mixture of said acids, provided that the fatty acid be at least 40 mole % of saturated or monounsaturated straight-chain fatty acid with at least 12 carbon atoms, with diethylene triamine, dipropylene triamine or mixtures thereof in a molar ratio of fatty acid to triamine of about 2:1 to form a bis-amide, heating the resulting fatty acid amine condensation product with urea in a molar ratio of about 1:0.5 to 1:1 so that 0.5 to 1 mole of ammonia per mole of fatty acid amine condensation product is given off, and finally, treating the resulting urea condensation product with 1 to 5 moles of formaldehyde per mole of urea to methylolate the urea condensation product.

2. The process of claim 1, wherein at least 40 mole % of the fatty acid consists of saturated or monounsaturated straight-chain fatty acids with at least 14 carbon atoms.

3. The process of claim 1, wherein the fatty acid is a mixture of fatty acids having 12 to 24 carbon atoms.

4. The process of claim 1, wherein the fatty acid is condensed with diethylene triamine.

* * * * *